US00PP27376P3

(12) United States Plant Patent
Robacker et al.

(10) Patent No.: US PP27,376 P3
(45) Date of Patent: Nov. 15, 2016

(54) ***VITEX AGNUS-CASTUS* PLANT NAMED 'V07-2'**

(50) Latin Name: *Vitex agnus-castus*
Varietal Denomination: V07-2

(71) Applicant: University of Georgia Research Foundation, Inc., Athens, GA (US)

(72) Inventors: Carol D. Robacker, Peachtree City, GA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 111 days.

(21) Appl. No.: 14/544,229

(22) Filed: Dec. 10, 2014

(65) Prior Publication Data

US 2016/0174443 P1 Jun. 16, 2016

(51) Int. Cl.
*A01H 5/02* (2006.01)

(52) U.S. Cl.
USPC ..... Plt./226

(58) Field of Classification Search
USPC ..... Plt./226, 216
See application file for complete search history.

*Primary Examiner* — June Hwu
(74) *Attorney, Agent, or Firm* — Klarquist Sparkman, LLP

(57) ABSTRACT

The *Vitex agnus-castus* plant is of short height, has a compact form and pink flowers.

3 Drawing Sheets

Genus and species: *Vitex agnus-castus*.

Varietal denomination: The new *Vitex agnus-castus* claimed is of the cultivar denominated 'V07-2'.

BACKGROUND OF THE INVENTION

The present invention relates to a new and distinct cultivar of *Vitex agnus-castus* hereinafter referred to by the varietal domination 'V07-2'.

Pedigree and history: 'V07-2' originated from a cross of *Vitex agnus-castus* 'Salinas Pink' (unpatented, female parent) and *Vitex agnus-castus* 'Abbeville Blue' (unpatented, male parent) made in 2006 under the direction of David Knauft. Seedlings from this cross were grown in a field plot in Watkinsville, Ga. In 2006, a single plant, initially labeled 03-06, was identified and selected. This selected plant had deep pink flowers and an attractive form. Cuttings were made from this plant, and distributed to Carol Robacker, who took over this breeding program in 2009. This selection was given the cultivar name 'V07-2', and plants of this cultivar were planted in a replicated field plot (three reps, randomized block design) in Griffin, Ga. in the fall of 2009. 'V07-2' has been grown in an irrigated field plot in Griffin, Ga. Plants have been fertilized annually in the spring.

Mean panicle lengths and number of panicles per compound panicle were counted each summer. First bloom and re-bloom dates were noted each year. Data was collected on leaf yellowing, leaf drop, thinning, and leaf spot in July, August and September of each year.

'V07-2' has been grown in an irrigated field plot in Griffin, Ga. Plants have been fertilized annually in the spring. The height of these plants after five summers' growth averaged about 2.9 m. Stems are RHS (Royal Horticultural Society, 2001) brown N199A or 199B when older, round, with dense minute curved hairs and scattered longer curved hairs.

The trunk color is a mix of greyed-white 156A and grey-brown 199D. Stem striations begin on large stems or trunks at about 2.5 cm diameter, with cracking and exfoliation noticeable at about 5 cm diameter. Leaves emerge with a green 137C upper surface, changing to a deeper green 137A during the summer, and becoming yellow-green 146A in the fall. Lower leaf surface is greyed-green 191B throughout the season.

Leaves are palmately-compound, typically about 13 cm×14 cm, with mostly seven leaflets. Margins are entire, with acute apices and bases. The upper leaf surface has many scattered hairs, slightly glandular, while the lower surface is more densely pubescent and very glandular. Leaves are slightly waxy above, dull underneath. Venation is simple. Leaf arrangement on stems is opposite.

Flower buds are red-purple 65C. Flowers occur in an elongated compound panicle, 22 to 26 cm long. At emergence, flowers are red-purple N74D, and become a darker red-purple N74C at full bloom. The peduncle is grayed-green 193A. The number of individual flowers per inflorescence ranges from 254 to 632. Sepals are greyed-green 198A.

SUMMARY OF THE INVENTION

'V07-2' plants have been evaluated for four years at the Griffin, Ga. site. Height and width data has been collected annually. Cold damage was assessed each spring. Mean panicle lengths and number of panicles per compound panicle were counted each summer. First bloom and re-bloom dates were noted each year. Data was collected on leaf yellowing, leaf drop, thinning, and leaf spot in July, August and September of each year.

'V07-2' plants from cuttings were was planted into a field plot in Griffin, Ga. in June 2009. A 'Salinas Pink' was planted into the same plot in June 2011. All data in the Tables are from rooted liners grown in one-gallon containers. Data given are averages of measurements made on three plants of 'V07-2' and one plant for 'Salinas Pink'.

The following characteristics have been consistently observed in the original plant of this new variety and in asexually propagated progeny grown from stem (softwood) cuttings in Griffin, Ga., and, to the best knowledge of the inventors, their combination forms the unique characteristics of 'V07-2' as a new and distinct cultivar. Asexual propagation by stem cuttings has proven that these characteristics are firmly fixed in succeeding asexually propagated generations.

1. Short height (Table 1);
2. Compact form (FIG. 3);
3. Dark pink flowers (FIG. 2).

'V07-2' is an improved pink *Vitex* as compared to the industry standard 'Salinas Pink', the only commonly available pink *Vitex*.

Comparison. Height and width were measured annually. 'Salinas Pink' is a taller and wider plant than 'V07-2'; (Table 1). Both 'V07-2' and 'Salinas Pink' begin flowering at the same time each year (Table 2). Both have moderate repeat blooming during summer and fall (Table 3). Panicles on 'V07-2' are generally a bit shorter, but with greater diameter than those on 'Salinas Pink' (Table 4, FIG. 1). Flowers of 'V07-2' are a slightly darker pink than those of 'Salinas Pink' (FIG. 2). The flowers of 'Salinas Pink' and of 'V07-2' have one larger anterior petal and four smaller petals. A comparison was made of sample 'Salinas Pink' and 'V07-2' flowers with the following results. The inside of the 'V07-2' anterior petal is Red-purple N74B or N74C, the inside of the other four petals is Red-purple N74D, the outer side of the petals is Purple 75B; and the inside of the 'Salinas Pink' anterior petal is Red-purple N74C or N74D, the inside of the other four 'Salinas Pink' petals is Purple 75B or 75C, and the outer side of the 'Salinas Pink' petals is Purple 75D. 'V07-2' has a rounded, compact form, while 'Salinas Pink' is very irregular in growth habit (FIG. 3). 'Abbeville Blue' has flowers that have a blue coloration.

'V07-2' is an improved pink Vitex, as compared to the industry standard, 'Salinas Pink', 'V07-2' is shorter in height (Table 1); has a more compact form (FIG. 3); and has slightly darker pink flowers (FIG. 2).

*Vitex agnus-castus* is a deciduous shrub or small tree used in landscapes. This drought tolerant plant may be grown in cold hardiness zones 6 through 9. During cold winters in zone 6, it may die back to the ground, but will likely re-grow from the roots and produce a flowering shrub during the following summer, as flower buds are formed on new growth. Late spring freezes in zone 7 may also cause cold damage and dieback, but the plants recover and bloom during the summer.

'V07-2' has been and is propagated vegetatively by stem cuttings.

TABLE 1

Height and width (cm) of *Vitex* 'V07-2' and 'Salinas Pink' one, two and three years after planting in a field plot in Griffin, Georgia. Data for 'V07-2' is the average of three plants.

| Entry | Year 1 | Year 2 | Year 3 |
|---|---|---|---|
| 'V07-2' | 145 H × 222 W | 172 H × 236 W | 245 H × 292 W |
| 'Salinas Pink' | 118 H × 142 W | 228 H × 291 W | 297 H × 370 W |

TABLE 2

Flowering characteristics of V07-2 and 'Salinas Pink' grown in Griffin, Georgia.

| Entry | First bloom 2011 | First bloom 2012 | First bloom 2013 |
|---|---|---|---|
| 'V07-2' | 5-30 | 5-14 | 6-10 |
| 'Salinas Pink' | — | 5-14 | 6-10 |

TABLE 3

Repeat flowering in July, August, September and October in 2011, 2012, and 2013.

| Entry | Year | July | August | September | October |
|---|---|---|---|---|---|
| 'V07-2' | 2011 | 0* | 1.7 | 2.2 | 0 |
| | 2012 | 1.3 | 3.0 | 4.0 | 0.7 |
| | 2013 | 0.7 | 0.3 | 1.3 | 1.2 |
| 'Salinas Pink' | 2011 | 0 | 1.0 | 3.0 | 2.0 |
| | 2012 | 2.0 | 3.0 | 3.0 | 2.0 |
| | 2013 | 1.0 | 0 | 0.5 | 0.5 |

*Repeat flowering was rated using the following scale: 0 = no flowering; 1 = 10% full bloom; 2 = 20 to 30% full bloom; 3 = 40 to 50% full bloom; 4 = at least 60% full bloom.

TABLE 4

Panicle length, diameter and number of sub-panicles per panicle averaged over 2011, 2012, and 2013. Measurements were made on four typical or average-sized panicles per plant per year.

| Entry | Mean Panicle length (cm) | Mean Panicle diameter (cm) | Number of subpanicles/panicle |
|---|---|---|---|
| 'V07-2' | 22.5 | 4.4 | One long, two to four short |
| 'Salinas Pink' | 24.1 | 3.2 | One long, two to four short |

BRIEF DESCRIPTION OF THE FIGURES

The accompanying colored photographic illustrations show the overall appearance and distinct characteristics of the new cultivar of *Vitex agnus-castus*. The colors in the photographs are as close as possible with the photographic and printing technology utilized.

DETAILED BOTANICAL DESCRIPTION

Figure 1:
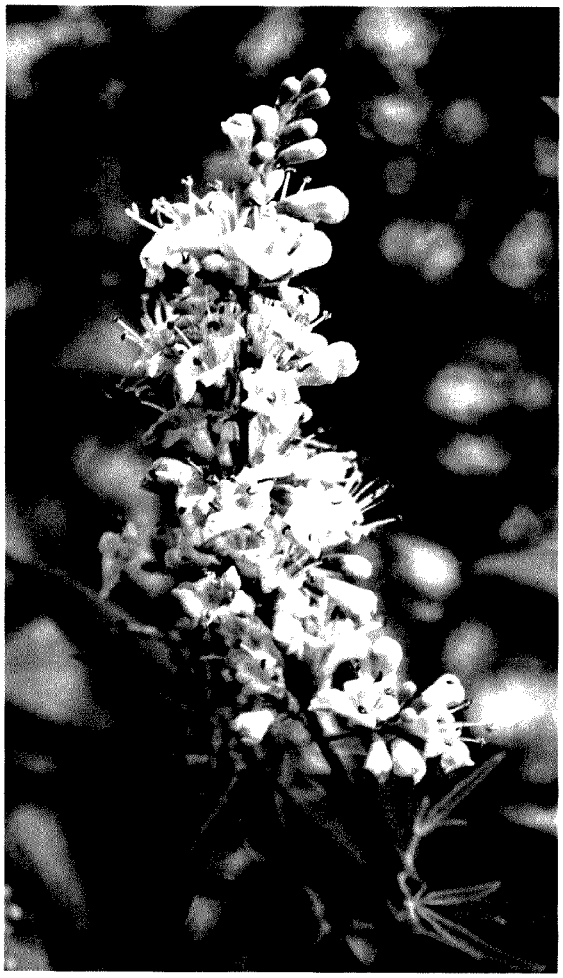
FIG. 1 is a photograph of the new variety 'V07-2' (left image) during flowering in Griffin, Ga. and a photograph of 'Salinas Pink' (right image). 'V07-2' has slightly darker pink flowers with a wider diameter than 'Salinas Pink'. 'Salinas Pink' has slighter longer panicles.
Figure 1:
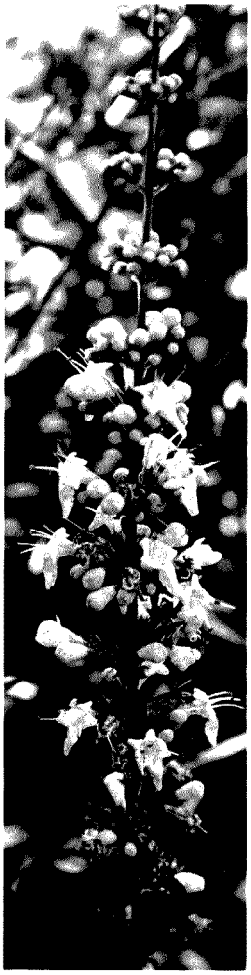
Figure 2:
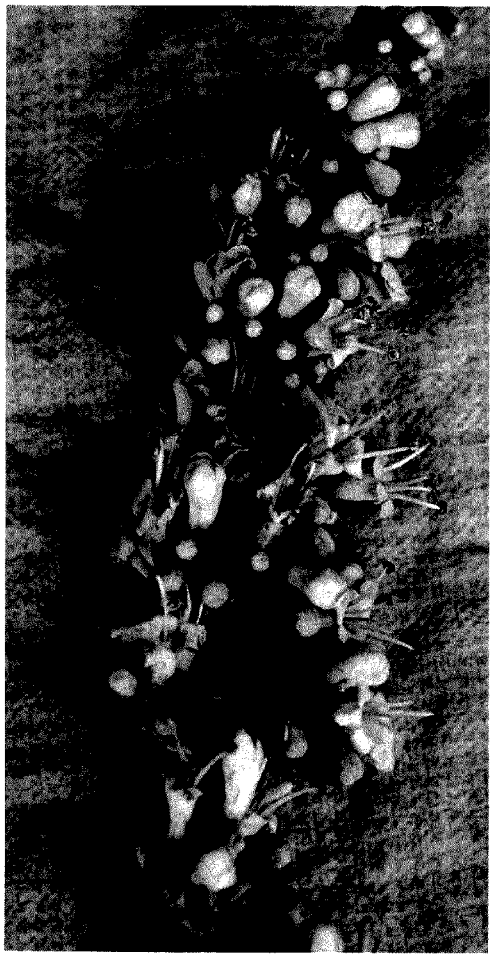
FIG. 2 is a close up of flowers of the new variety 'V07-2' during flowering in Griffin, Ga. on the left, and 'Salinas Pink' on the right, taken from flower clusters of similar blooming stage.
Figure 2:
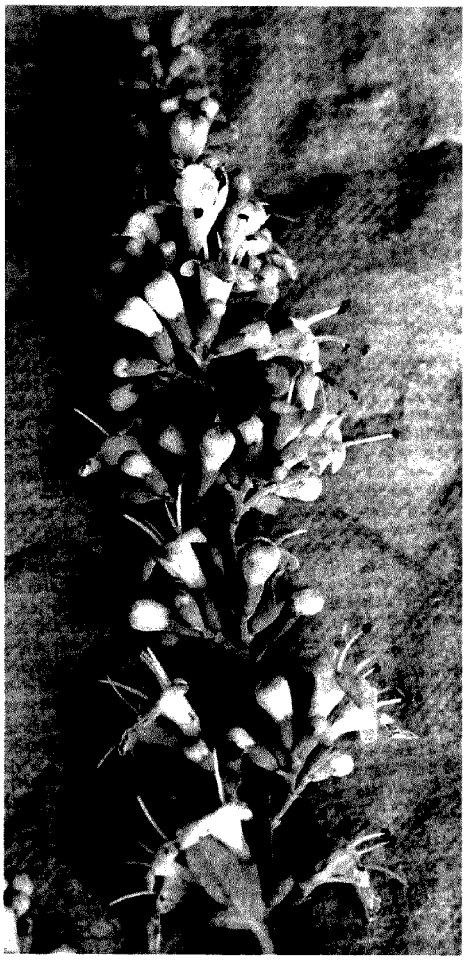
Figure 3:
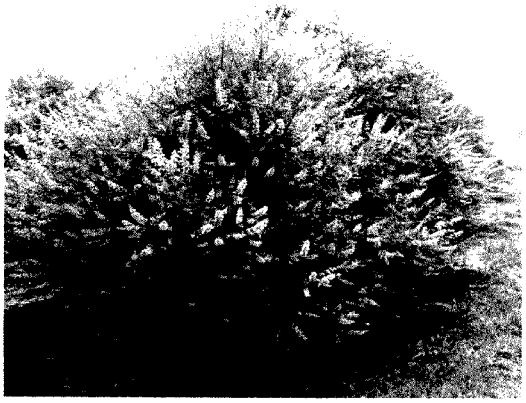
FIG. 3 is a photograph of 'V07-2' (left image) and 'Salinas Pink' (right image) in peak bloom in Griffin, Ga. The form on 'V07-2' is more compact and rounded, while 'Salinas Pink' has an irregular form.
Figure 3:
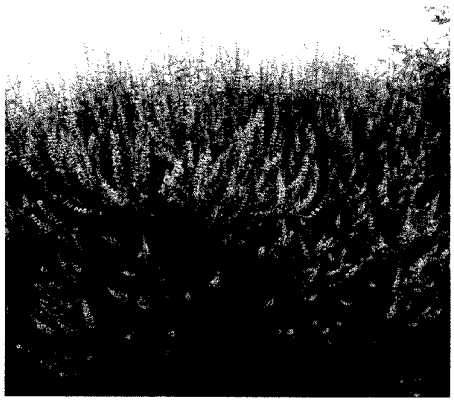

The following is a detailed description of the *Vitex agnus-castus* cultivar named 'V07-2'. Data was collected in Griffin, Ga. from three year old plants grown from cuttings and growing outdoors. 'V07-2' has not been tested under all possible conditions hence, phenotypic differences may be observed with variations in environmental conditions without any variance in genotype.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society (R.H.S.), London, England. This description is from observations of typical three year old plants growing in Griffin, Ga.

Parentage:

*Female parent*.—'Salinas Pink'.

*Male parent*.—'Abbeville Blue'.

Size: 245 cm tall by 292 cm wide, measured at highest and widest point. Size is reflective of habit, i.e., 2' by 3' is rounded to broad-rounded.

Habit: Open, spreading, upright.

Texture: Medium coarse.

Stems:

*First year*.—Color: Grey-Brown N199A. Diameter: 4-5 mm. Pubescence: dense minute curved hairs, scattered longer curved hairs. Exfoliation: none. Shape: Round. Pith: Type: Solid. Diameter: 3 mm. Color: Yellow-Green 150D. Odor: strong, spicy, acrid. Internode Length: 6.5 cm.

*Second year*.—Color: Mix of Grey-Brown 199B and Brown N200B. Diameter: approx. 6 mm. Exfoliation: none.

Vegetative buds:

*Arrangement*.—Opposite.

*Type*.—Valvate.

*Size*.—1 mm×1 mm.

*Scale number*.—2.

*Scale color*.—Greyed-Orange 177C.

*Position/disposition*.—45°.

*Number at node*.—2, one on each side.

*Pubescence*.—Scattered short hairs.

*Shape*.—Domed, rounded, mostly covered by bud scales.

Leaf scar:

*Shape*.—Cup shaped.

*Vascular bundle traces*.—3, horizontal.

*Pubescence*.—Dense minute airs around perimeter.

*Position of bud*.—Just above.

*Color differentiation*.—Yellow-Green 144A.

*Size*.—2×3 mm.

Trunk or large stems:

*Color(s)*.—Mix of Greyed-White 156A and Greyed-Brown 199D.

*Size stem exfoliation begins on*.—Approximately 5 cm.

*Diameter*.—2.5 to 5.0 cm.

*Texture*.—Striations start at 2.5 cm, cracking by 5.0 cm.

Leaf:

*Color through seasons*.—Emerging dates — mid April. Upper: Green 137C. Lower: Greyed-Green 191B. Summer dates — mid July. Upper: Green 137A. Lower: Greyed-Green 191B. Fall dates — September. Upper: Yellow-Green 146A. Lower: Yellow-Green 191B.

*Mature size*.—13 cm×14 cm.

*Apex*.—Acute.

*Base*.—Acute.

*Margin*.—Mostly entire.

*Shape*.—Palmate, mostly 7 leaflets. Lobes: None. Sinuses: none.

*Vein color*.—Yellow-Green 147D.

*Pubescence*.—Upper surface has many scattered hairs, with more along the veins, slightly grandular surface. Lower leaf is more densely hairy and has a very grandular surface.

*Arrangement on stem*.—Opposite.

*Venation*.—Simple.

*Texture*.—Thickness: 0.4 mm. Degree of waxiness of surfaces: slightly waxy on upper surface, dull on lower.

Average leaflet size: The leaflets of five leaves that had five leaflets per leaf were measured. The leaflets are arranged palmately, going from small to medium to large to medium to small.

*Mean lengths and widths of each of the five measured leaflets are as follows*.—57.6 mm long, 9.2 mm wide; 78.8 mm long, 14.0 mm wide; 91.4 mm long, 14.4 mm wide; 75.8 mm long, 13.2 mm wide; 56.6 mm long, 9.2 mm wide.

Petiole:

*Length*.—4.3 cm.

*Shape*.—Round.

*Color*.—Upper Greyed-Orange 177A, lower Yellow-Green 145B with some Greyed-Orange N167A.

*Pubescence*.—Densely covered in minute slightly curved hairs.

*Diameter*.—1.7 mm.

Flower buds:

*Size (l×w)*: 5 mm×3.5 mm.

*Color*.—Red-Purple 65C.

*Shape*.—Teardrop.

*Pubescence*.—Glandular surface, tomentose.

*Time of full maturity (first visible)*.—Early summer.

*Time range for showiness*.—Mid May through September.

Flower

*Inflorescence(s)*.—Type: elongated panicle, compound, slightly whorled. Size (1 x w): 22-26 cm x 2.0-4.4 cm. Color: At emergence (date) — Red-Purple N74D. Full bloom (date) — Red-Purple N74C. Fading (date) — Red-Purple 63D with Red-Purple N74B.

*Peduncle*.—Color: Greyed-Green 193A. Pubescence: glandular, tomentose. Number of individual flowers per inflorescence: 254-545, 315-632. Average length: 45.2 mm.

*Petal(s)*.—Size: 10 mm×8 mm. Shape: zygomorphic, gamopetalous, bilabiate, large anterior petal and four smaller petals. Apex: 5 lobes rounded and slightly curled. Base: funnel. Margin: slightly curled. Pubescence: mostly glabrous, scattered glandular with thick tuft of hairs inside base and many glandular hairs outside. Texture: mostly smooth, slightly punctate. Color at peak of bloom: The inside of the large anterior petal is Red-purple N74B or N74C. The inside of the other four petals is Red-purple N74D. The outside of the petals is Purple 75B.

*Pedicels*.—Color (RHS) — Greyed-Green 193A. Pubescence — glandular, tomentose. Length — 2-3 mm.

*Sepal(s)*.—Size (l×w): 3 mm×2 mm. Shape: united, slightly lobed. Apex: slightly lobed. Base: united, short tubular. Margin: smooth. Pubescence: glandular, tomentose, canescent. Texture: hoary. Color at peak of bloom: Upper surface — Greyed-Green 198A with traces of Violet-Blue 94A. Lower surfaces — lower Yellow-Green 144C with Violet-Blue 93C.

*Male reproductive structures*.—Number: 4. Anther: Size (l×w) — 1 mm×0.5 mm. Color — White 155C. Filament: Size (l×w) — 5.5 mm×0.5 mm. Color — Red-Purple 69D. Pollen color — White 155C. Pubescence — scattered short hairs along the filament and a thick tuft of hairs at base.

*Female reproductive structures*.—Pistil: Shape — tubular, bifid. Size (l×w) — 6 mm×0.5 mm. Position (superior, inferior, etc.) — superior. Color (RHS) — Violet 84B. Pubescence — thickly tufted hairs at base. Stigma: Shape — round, bifid. Color (RHS) — White 155C. Pubescence — none. Style: Length — 6 mm. Shape — tubular, forked at stigma (bifid). Color (RHS) — Violet 84B. Pubescence — glabrous, tufted at base. Ovary: Shape — round. Number — 1. Pubescence — scattered short hairs, numerous glands present on surface.

Fruit:

*Type*.—Drupe-like.

*Size* (*l*×*w*).—4 mm×3 mm.

*Color*(*s*) *during ripening*.—Early (date) — Yellow-Green 146D. Mid (date) — Grey-Brown 199A and Grey-Brown 199B. Late (date) — Brown 200D and Brown 200A.

*Shape*.—Globular.

*Number per infructescence*.—1.

*Pubescence*.—Few scattered hairs, surface lightly punticulate.

*Number of carpels*.—2.

*Persistence* (*effective period*).—Mid to late summer through fall into winter.

Seed:

*Shape*.—Globular.

*Size*.—4 mm×3 mm.

*Color*.—Brown 200A when fully ripe.

*Number per locule per ovary per fruit*.—1.

*Germination capacity*.—≈30%.

*Pubescence*.—Scattered minute hairs.

Pest and disease resistance: Not observed to date.

What is claimed is:

1. A new and distinct cultivar of the *Vitex agnus-castus* plant named 'V07-2' substantially as illustrated and described herein.

* * * * *

'V07-2'

'Salinas Pink'

'V07-2'

'Salinas Pink'

'V07-2'

'Salinas Pink'